(12) United States Patent
Suehara et al.

(10) Patent No.: US 7,534,989 B2
(45) Date of Patent: May 19, 2009

(54) DETECTING DEVICE AND LAMINATED BODY MANUFACTURING APPARATUS EMPLOYING SUCH DETECTING DEVICE

(75) Inventors: Kazuyoshi Suehara, Fujinomiya (JP); Ryo Mori, Fujinomiya (JP); Nobuyasu Akiyoshi, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 52 days.

(21) Appl. No.: 11/631,783

(22) PCT Filed: Jul. 6, 2005

(86) PCT No.: PCT/JP2005/012882

§ 371 (c)(1),
(2), (4) Date: Jan. 8, 2007

(87) PCT Pub. No.: WO2006/004227

PCT Pub. Date: Jan. 12, 2006

(65) Prior Publication Data

US 2008/0030734 A1 Feb. 7, 2008

(30) Foreign Application Priority Data

Jul. 6, 2004 (JP) .............................. 2004-199897

(51) Int. Cl.
*G06M 7/00* (2006.01)
*G01N 21/86* (2006.01)

(52) U.S. Cl. .................................. 250/221; 250/559.42

(58) Field of Classification Search . 250/559.4–559.45, 250/559.22, 221; 356/430, 238.1–238.3, 356/239.1, 239.2, 239.3, 239.7, 239.8, 237.2, 356/237.3
See application file for complete search history.

(56) References Cited

U.S. PATENT DOCUMENTS

| | | | | |
|---|---|---|---|---|
| 5,095,214 A | * | 3/1992 | Eder | ...................... 250/559.03 |
| 5,701,180 A | | 12/1997 | Saindon et al. | |
| 2002/0110269 A1 | | 8/2002 | Floeder et al. | |

FOREIGN PATENT DOCUMENTS

| | | | |
|---|---|---|---|
| JP | 11-034280 | * | 2/1999 |
| JP | 11-34280 A | | 2/1999 |
| JP | 11-188830 A | | 7/1999 |
| JP | 2003 062906 A | | 3/2003 |

* cited by examiner

*Primary Examiner*—Que T Le
*Assistant Examiner*—Pascal M Bui-Pho
(74) *Attorney, Agent, or Firm*—Sughrue Mion, PLLC

(57) ABSTRACT

A laser beam emitted from a laser diode of each of detectors is applied to a partly cut region of a photosensitive sheet film which is spread toward the detectors by a film bending roller. Part of the laser beam which is reflected from the partly cut region is detected by an amount-of-light sensor. The laser beam that is applied to a surface of the photosensitive sheet film other than the partly cut region is reflected outside of a light-detecting area of the amount-of light sensor, and is not detected by the amount-of-light sensor.

20 Claims, 9 Drawing Sheets

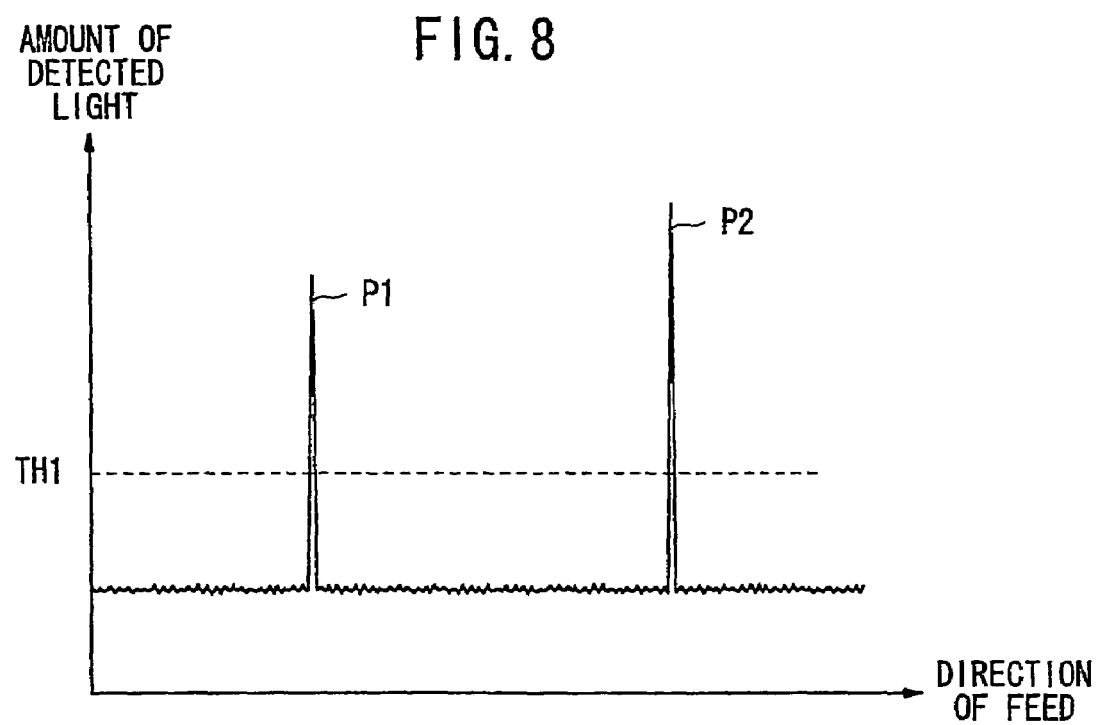

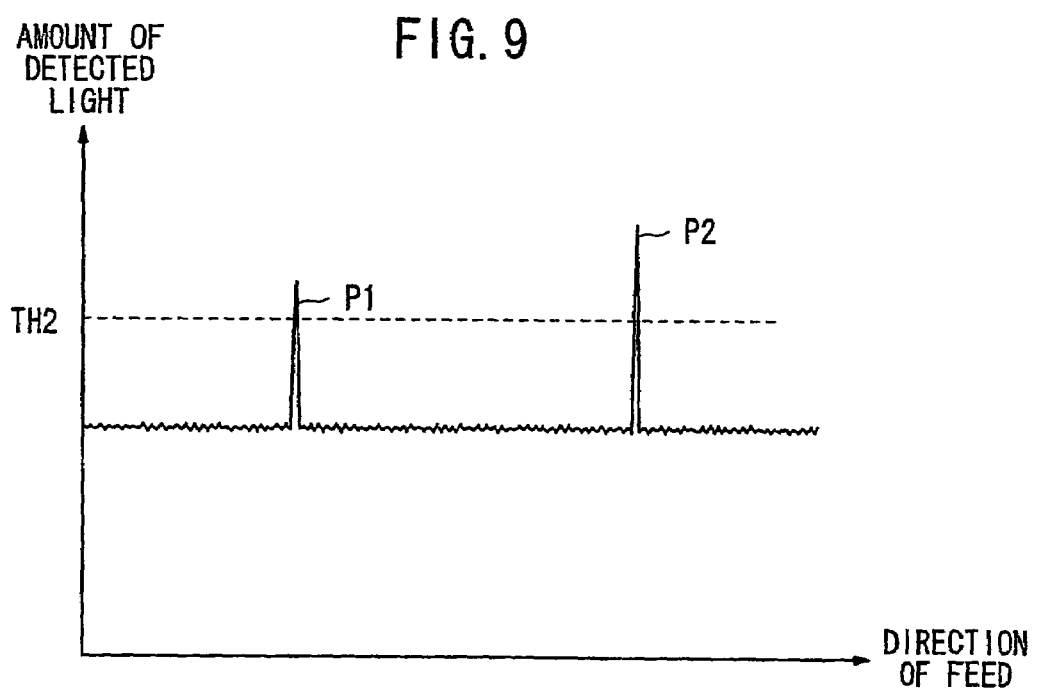

DETECTING DEVICE AND LAMINATED BODY MANUFACTURING APPARATUS EMPLOYING SUCH DETECTING DEVICE

TECHNICAL FIELD

The present invention relates to a detecting device for detecting a recess defined in a sheet, and a laminated body manufacturing apparatus which employs such a detecting device.

BACKGROUND ART

Photosensitive laminated body manufacturing apparatus are employed to manufacture a photosensitive laminated body by pressing a photosensitive pigment dispersion (photosensitive material layer) applied to a light-permeable base film (support) against a glass substrate or a resin substrate. The photosensitive laminated body is thus constructed of the glass substrate or the like with the photosensitive material layer transferred thereto. After the support is peeled off from the photosensitive laminated body, the photosensitive laminated body is exposed to a certain pattern and then developed by photolithography. The same process is performed on photosensitive films having photosensitive material layers of different colors. In this manner, color filter substrates for liquid crystal panels or organic EL panels are manufactured.

For continuously manufacturing such photosensitive laminated bodies, an elongate photosensitive web comprising a photosensitive material layer and a protective film that are successively deposited on a support is supplied, and then the protective film is transversely cut off, leaving the support, at partly cut regions spaced by intervals based on the size of a glass substrate. Thereafter, portions of the protective film which corresponds to glass substrates are successively peeled off from the partly cut regions, exposing lengths of the photosensitive material layer which are pressed against the respective glass substrates thereby producing a plurality of successive photosensitive laminated bodies. The photosensitive laminated bodies are then separated by peeling the support off from the photosensitive material layer. For details of the manufacturing process, reference should be made to Japanese Laid-Open Patent Publication No. 11-34280 and Japanese Laid-Open Patent Publication No. 11-188830.

In order to produce high-quality photosensitive laminated bodies, each of the lengths of the photosensitive material layer needs to be accurately pressed against a glass substrate at a given position thereon based on the partly cut regions from which the protective film has been peeled off. Consequently, it is necessary to detect the partly cut regions in advance, and control highly accurately the timing to press the length of the photosensitive material layer against the glass substrate.

However, since the partly cut regions are formed by a sharp cutter, it is extremely difficult to detect them with an ordinary photodetector or CCD camera. Though a highly sensitive sensor may be used to detect the partly cut regions, such a highly sensitive sensor tends to increase the cost of the photosensitive laminated body manufacturing apparatus.

According to Japanese Laid-Open Patent Publication No. 11-34280 and Japanese Laid-Open Patent Publication No. 11-188830, the rotational speed of a roller which supplies the elongate photosensitive web to the cutter for forming partly cut regions therein is detected by a rotary encoder, and the timing at which a partly cut region reaches a glass substrate is estimated from the detected rotational speed of the roller and controlled.

If the length of the elongate photosensitive web changes or if the web slips off the roller due to stretching, sagging, vibration, and frictional force variation of the elongate photosensitive web, then the accuracy of the fed length of the elongate photosensitive web based on the rotational speed of the roller which is detected by the rotary encoder is lowered, making it impossible to position a partly cut region highly accurately on a glass substrate at a given position thereon.

DISCLOSURE OF INVENTION

It is a general object of the present invention to provide a detecting device which is of a highly inexpensive and simple structure capable of reliably detecting a recess defined in a sheet.

Another object of the present invention to provide a laminated body manufacturing apparatus for highly accurately manufacturing a laminated body which comprises a substrate and a sheet laminated on the substrate in a predetermined region thereof.

With a detecting device according to the present invention, a sheet body is deformed to spread a recess defined therein, illuminating light is applied from an illuminating unit to the spread recess in the sheet body, and the illuminating light reflected from the recess is detected by a light-detecting unit and processed.

Since the illuminating light is reflected by the spread recess which is different from the other area of the sheet body, the recess is reliably detected from the illuminating light detected by the light-detecting unit even if the recess is narrow.

The recess may be spread by a deforming unit such as a roller, a bending member, or the like for pressing the sheet body from one surface thereof toward an opposite surface thereof which has the recess defined therein, or a pulling unit for pulling the sheet body. The deforming unit such as a roller, a bending member, or the like allows the recess to be detected while the sheet body is being fed. The roller may have a small diameter and the range of the sheet body which is held in contact with the roller may be large to spread the recess to a large extent for detecting the recess with increased accuracy.

The detecting device according to the present invention is capable of highly accurately detecting a partly cut region in the form of a recess cut into a laminated body which is made up of a plurality of laminated sheet layers or perforations formed in a sheet body.

The illuminating unit may comprise a laser to apply a laser beam to the sheet body, and the light-detecting unit for detecting the laser beam may be disposed in a position that is offset a predetermined distance from an area for detecting light reflected from a portion of the sheet body other than the recess. With this arrangement, the recess can be detected in a reduced noise environment. The accuracy with which the position of the recess is detected can be increased by minimizing the diameter of the spot of the laser beam applied to the sheet body.

The light-detecting unit may comprise an amount-of-light sensor for detecting an amount of the illuminating light reflected by the sheet body, a position sensor for detecting a position to which the illuminating light reflected by the sheet body is applied, or a one-dimensional or two-dimensional CCD sensor or the like for capturing image information based on the illuminating light reflected by the sheet body.

If the sheet body has a colored layer which is cut to form the recess, then since the difference between an amount of light reflected from the recess and an amount of light reflected from the area of the sheet body other than the recess is large, the recess is more reliably detected.

According to the present invention, there is also provided a laminated body manufacturing apparatus incorporating a detecting device for highly accurately detecting the position of a recess defined in a sheet body as described above. The laminated body manufacturing apparatus is capable of highly accurately manufacturing a laminated body having a sheet body laminated on a certain area of a substrate, based on the position of the recess.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF DRAWINGS

FIG. 8 is a diagram illustrative of measured values of an amount of light reflected from partly cut regions and detected by the detecting mechanism; and FIG. 9 is a diagram illustrative of measured values of an amount of light reflected from partly cut regions and detected by the detecting mechanism.

BEST MODE FOR CARRYING OUT THE INVENTION

Figure 1:
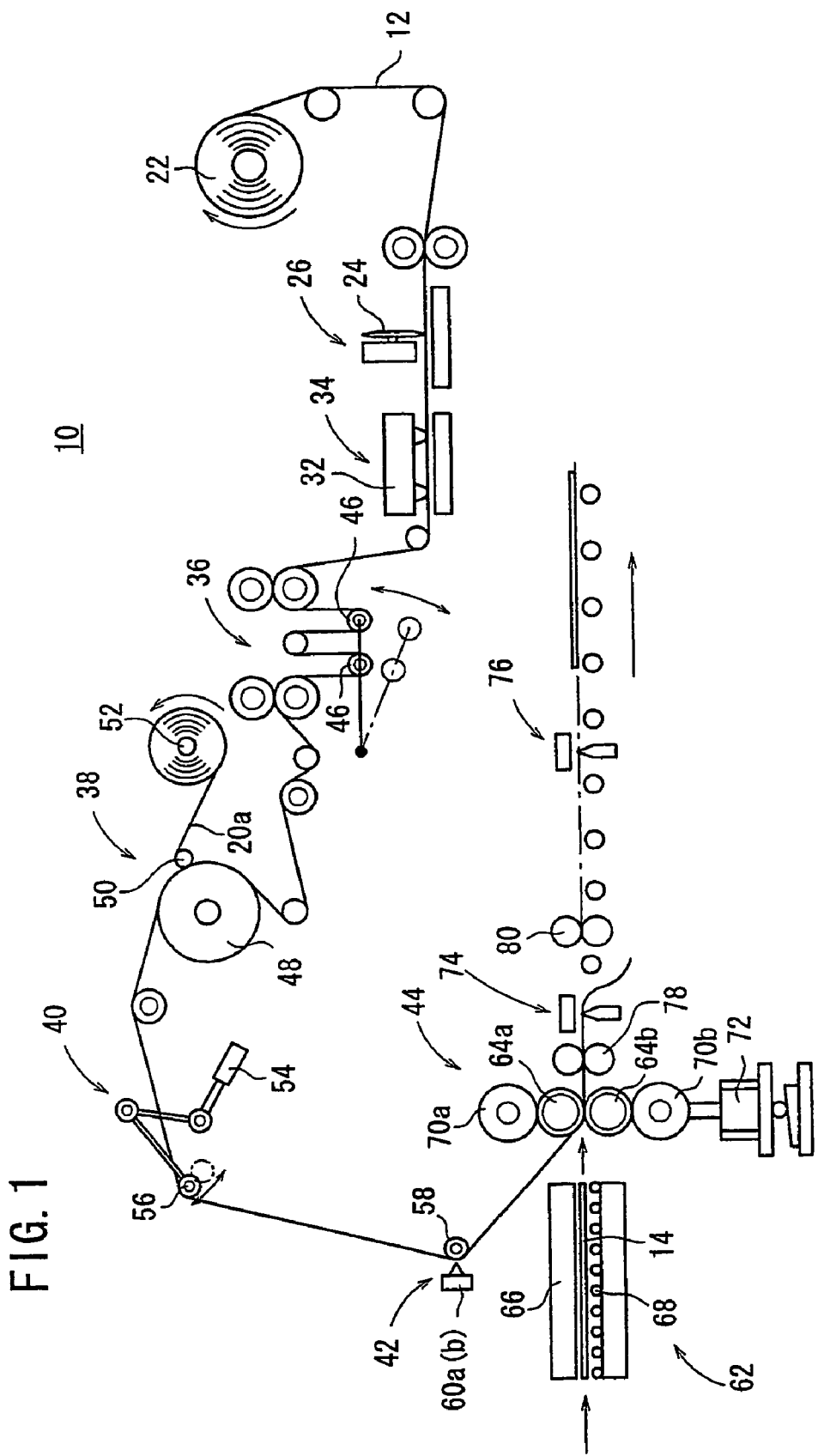
FIG. 1 is a schematic side elevational view of a photosensitive laminated body manufacturing apparatus according to an embodiment of the present invention.

FIG. 1 schematically shows a photosensitive laminated body manufacturing apparatus 10 according to an embodiment of the present invention. As shown in FIG. 1, the photosensitive laminated body manufacturing apparatus 10 is supplied with a photosensitive sheet film 12 (sheet body) having a laminated structure shown in FIG. 2 and a plurality of glass substrates 14. As shown in FIG. 3, the photosensitive sheet film 12 and the glass substrates 14 are pressed against each other, producing color filter substrates for liquid crystal panels or organic EL panels.

The photosensitive sheet film 12 comprises a base film 16, a photosensitive resin layer 18 having a certain color such as red, green, blue, or black, for example, and a protective film 20. The base film 16, the photosensitive resin layer 18, and the protective film 20 are laminated as a sheet body. The base film 16 is made of PET (PolyEthylene Terephthalate) and has an outer surface coated with an acrylic base coat agent including an antistatic additive. The photosensitive resin layer 18 is melted with heat at a temperature ranging from 80° to 150° C. by a pressing roller to be described later on, and transferred to the glass substrates 14. Partly cut regions 27a, 27b are formed as recesses in the photosensitive sheet film 12 at predetermined intervals by a circular blade to be described later on.

The photosensitive laminated body manufacturing apparatus 10 has a film roll 22 for supplying the photosensitive sheet film 12 and a processing mechanism 26 for transversely cutting certain portions of the protective film 20 and the photosensitive resin layer 18 of the supplied photosensitive sheet film 12, leaving the base film 16, thereby forming the partly cut regions 27a, 27b. The film roll 22 and the processing mechanism 26 are successively arranged from an upstream end of the photosensitive laminated body manufacturing apparatus 10.

Figure 2:
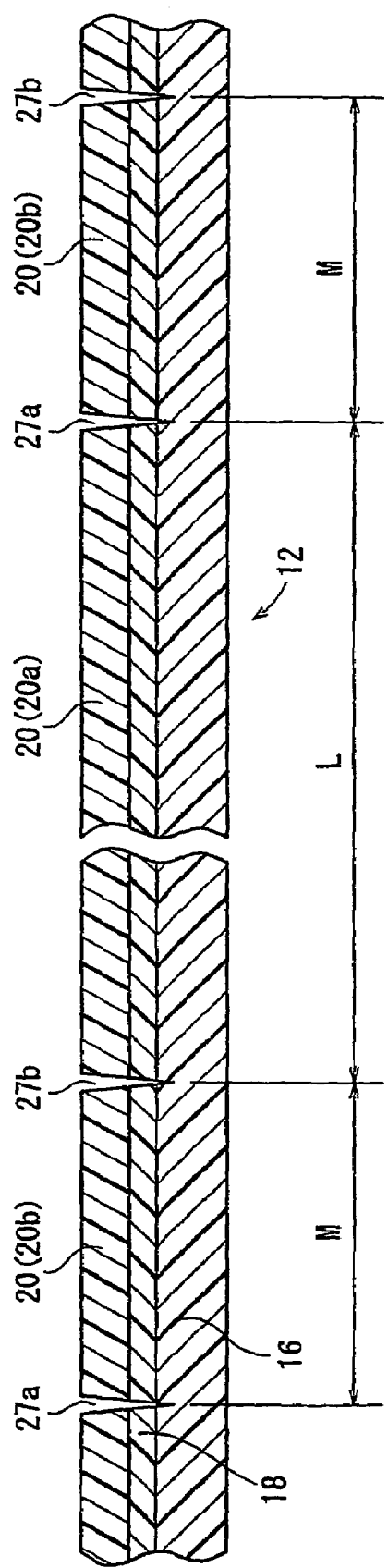
FIG. 2 is an enlarged fragmentary cross-sectional view of a photosensitive sheet film.
Figure 3:
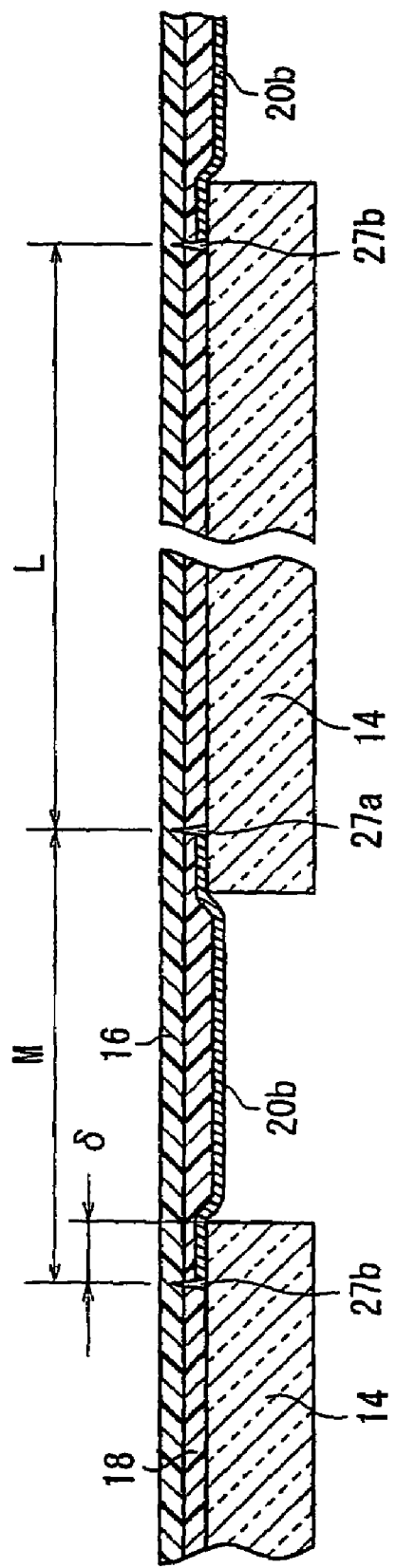
FIG. 3 is an enlarged fragmentary cross-sectional view of the photosensitive sheet film which is transferred to glass substrates.
Figure 4:
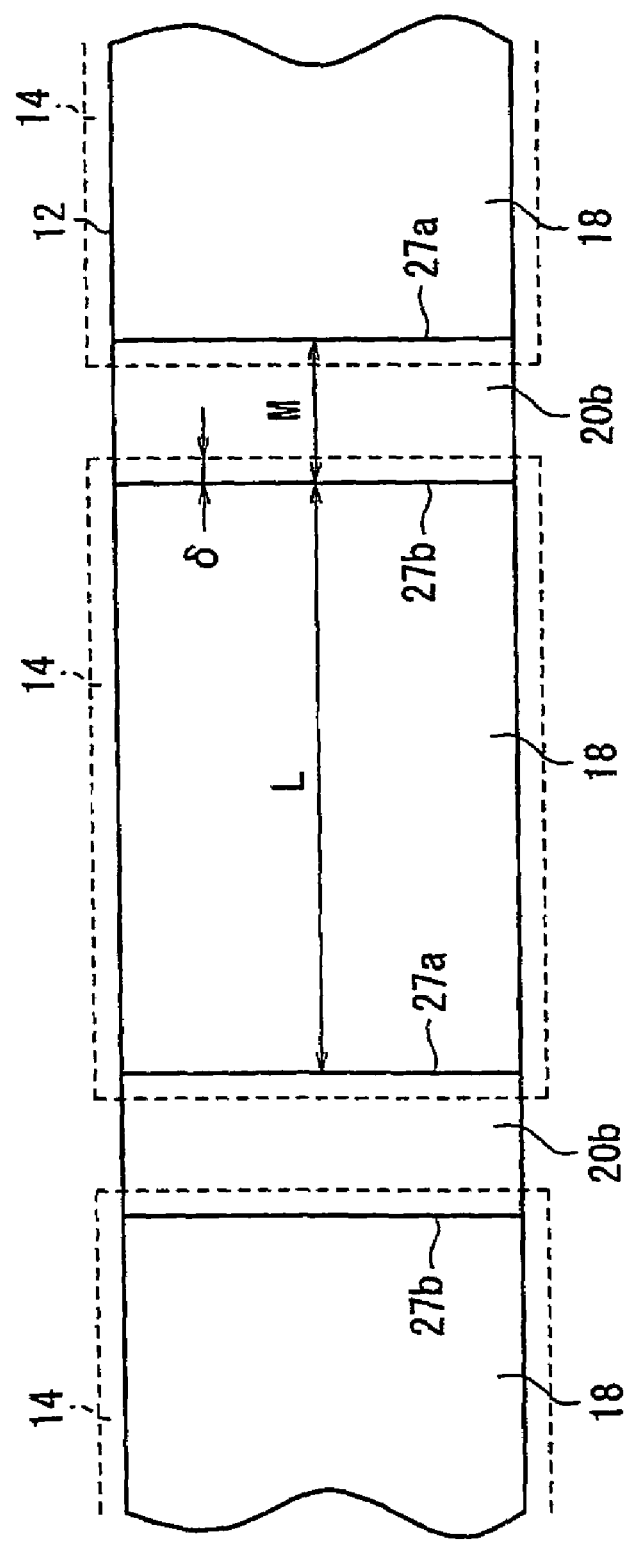
FIG. 4 is an enlarged fragmentary plan view of the photosensitive sheet film with partly cut regions formed therein.

The processing mechanism 26 has a circular blade 24 which travels transversely across the photosensitive sheet film 12 to form partly cut regions 27a, 27b in the protective film 20 and the photosensitive resin layer 18 at intervals that, as shown in FIGS. 2 through 4, correspond to a length L of the photosensitive resin layer 18 from which a protective film 20a is to be removed and which the photosensitive resin layer 18 is to be transferred to a glass substrate 14 and widths M of protective films 20b which are to be left on the glass substrate 14. The photosensitive resin layer 18 is transferred to an area of each of the glass substrates 14 whose opposite ends are spaced inwardly from the opposite ends of the glass substrate 14 by a distance δ.

As shown in FIG. 1, the processing mechanism 26 is followed downstream by a label bonding mechanism 34 having a suction pad 32 for attracting under suction a label (not shown) which has opposite ends that are to be bonded to protective films 20a positioned one on each side of a protective film 20b and an intermediate portion that is not to be bonded to the protective film 20b. The label bonding mechanism 34 serves to bond the opposite ends of the label to the protective films 20a.

Downstream of the label bonding mechanism 34, there are disposed a reservoir mechanism 36 for changing the feed mode of the photosensitive sheet film 12 from an intermittent feed mode to a continuous feed mode, a peeling mechanism 38 for peeling protective films 20a from the photosensitive sheet film 12, a tension control mechanism 40 for applying a predetermined tension to the photosensitive sheet film 12, a detecting mechanism 42 for detecting partly cut regions 27a, 27b which have been formed in the photosensitive sheet film 12 by the processing mechanism 26, and a pressure-bonding mechanism 44 for pressure-bonding the photosensitive resin layer 18 of the photosensitive sheet film 12 to glass substrates 14 with heat.

The reservoir mechanism 36 has a pair of rollers 46 which are vertically movable for absorbing a speed difference between the intermittent feed mode in which the photosensitive sheet film 12 is fed upstream of the reservoir mechanism 36 and the continuous feed mode in which the photosensitive sheet film 12 is fed downstream of the reservoir mechanism 36. The peeling mechanism 38 has a suction drum 48 for reducing tension variations of the photosensitive sheet film 12, and a peeling roller 50 disposed in the vicinity of the suction drum 48. The peeling roller 50 successively peels the protective films 20a off from the photosensitive sheet film 12, and the protective films 20a that are peeled off are wound by a takeup unit 52. The tension control mechanism 40 has a cylinder 54 which is actuated to angularly displace a tension dancer 56 for adjusting the tension of the photosensitive sheet film 12 which is trained around the tension dancer 56.

The detecting mechanism 42 serves as the detecting device according to the present invention. The detecting mechanism 42 has a film bending roller 58 (spreading means) disposed between the tension control mechanism 40 and the pressure-bonding mechanism 44 for bending the photosensitive sheet film 12 toward the protective film 20 to make the protective film 20 convex away from the film bending roller 58, and two detectors 60a, 60b for detecting the partly cut regions 27a, 27b of the photosensitive sheet film 12.

Figure 5:
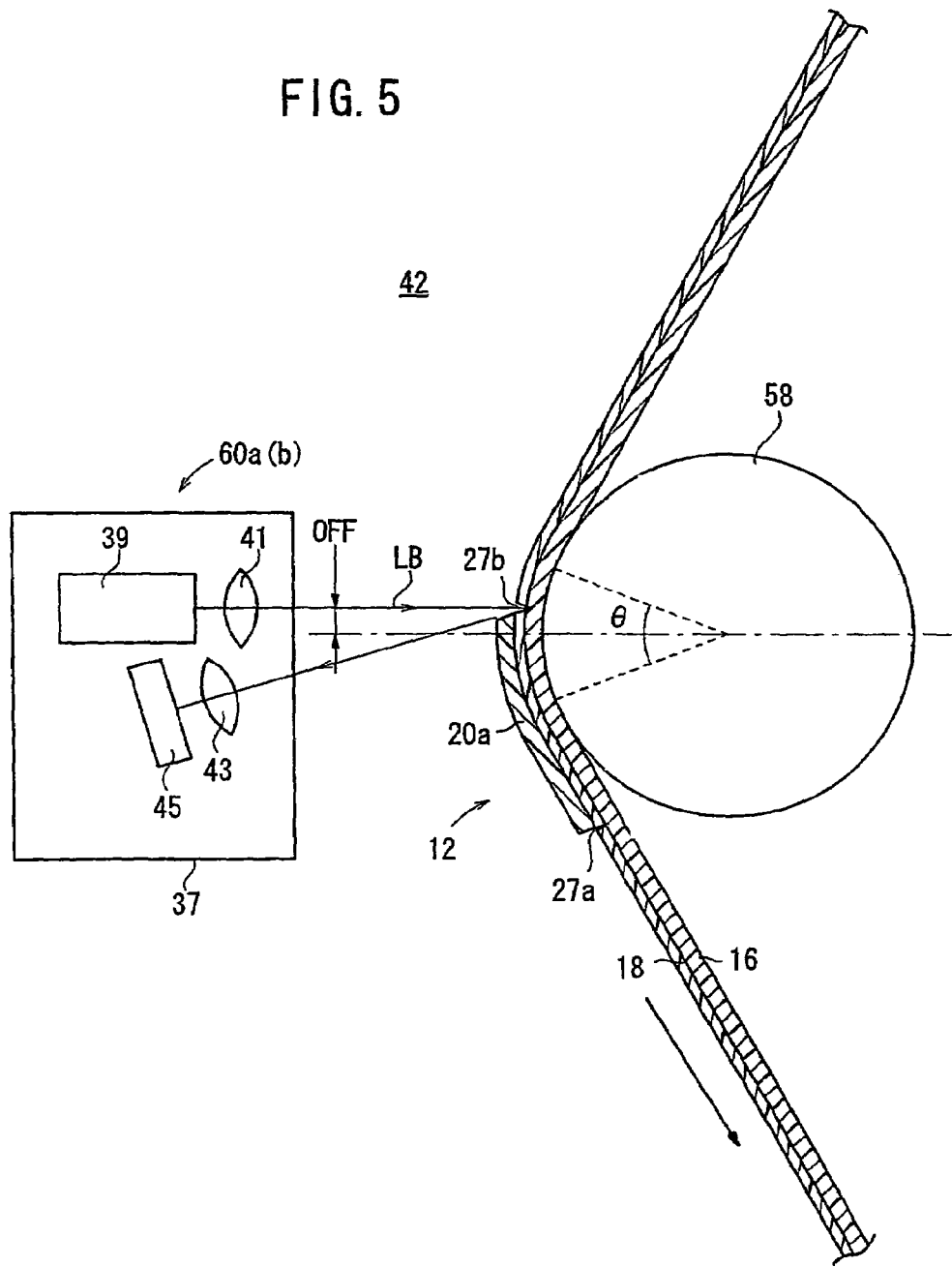
FIG. 5 is a schematic view of a detecting mechanism for detecting partly cut regions in the photosensitive laminated body manufacturing apparatus.

The two detectors 60a, 60b are spaced apart from each other in the direction in which the partly cut regions 27a, 27b extend transversely across the photosensitive sheet film 12. As shown in FIG. 5, each of the detectors 60a, 60b comprises a laser diode 39 (illuminating means) for emitting a laser beam LB, a collimator lens 41 for collimating the laser beam LB emitted from the laser diode 39, a condensing lens 43 for converging the laser beam LB which is reflected from the photosensitive sheet film 12, and an amount-of-light sensor 45 for detecting an amount of light of the laser beam LB that is applied from the condensing lens 43 to the amount-of-light sensor 45. The laser diode 39, the collimator lens 41, the condensing lens 43, and the amount-of-light sensor 45 are housed in a heat-insulating case 37 to protect themselves from heat generated by the pressure-bonding mechanism 44. The detectors 60a, 60b may additionally be water-cooled or air-cooled for better protection from heat.

To prevent the laser beam LB which is reflected by the surface of the photosensitive sheet film 12 from being applied to the amount-of-light sensor 45, each of the detectors 60a, 60b has a large wrap angle θ which is defined about the center of the film bending roller 58 by the length of the photosensitive sheet film 12 that is bent by and held in contact with the film bending roller 58. Also, the optical axis of the laser beam LB applied from the collimator lens 41 to the photosensitive sheet film 12 is offset a predetermined distance OFF from the center of the film bending roller 58 toward the tension control mechanism 40. The photosensitive sheet film 12 may alternatively be offset from the center of the film bending roller 58 toward the pressure-bonding mechanism 44.

The pressure-bonding mechanism 44 which is disposed downstream of the detecting mechanism 42 has a pair of pressure-bonding rollers 64a, 64b for pressure-bonding, with heat, the photosensitive resin layer 18 of the supplied photosensitive sheet film 12 to the upper surface of a glass substrate 14 that is supplied from a substrate feed mechanism 62. The substrate feed mechanism 62 comprises a substrate heater 66 for sandwiching and heating the glass substrate 14 and a feeder 68 for feeding the glass substrate 14.

The pressure-bonding rollers 64a, 64b of the pressure-bonding mechanism 44 comprise heating rollers for pressure-bonding the photosensitive sheet film 12 and the glass substrate 14 to each other and heating them at a temperature ranging from 80° to 150° C. The pressure-bonding rollers 64a, 64b have respective rubber layers on their outer circumferential surfaces. The pressure-bonding mechanism 44 also has a pair of backup rollers 70a, 70b positioned above and below and held in rolling contact with the pressure-bonding rollers 64a, 64b, respectively. The backup roller 70b which is positioned below the backup roller 70a is pressed toward the upper backup roller 70a by an elevating mechanism 72.

The pressure-bonding mechanism 44 is followed downstream by a leading end cutting mechanism 74 for cutting off the leading end of the photosensitive sheet film 12 when the photosensitive laminated body manufacturing apparatus 10 starts to operate, and an inter-substrate cutting mechanism 76 for cutting the photosensitive sheet film 12 between two adjacent substrates 14. Film feed rollers 78 for drawing the photosensitive sheet film 12 when the photosensitive laminated body manufacturing apparatus 10 starts to operate are disposed between the pressure-bonding rollers 64a, 64b and the leading end cutting mechanism 74. Substrate feed rollers 80 for feeding a glass substrate 14 to which the photosensitive sheet film 12 is bonded are disposed downstream of the leading end cutting mechanism 74.

The photosensitive laminated body manufacturing apparatus 10 according to the present embodiment is basically constructed as described above. Operation and advantages of the photosensitive laminated body manufacturing apparatus 10 will be described below.

The photosensitive sheet film 12 that is unreeled from the film roll 22 is fed to the processing mechanism 26. In the processing mechanism 26, the circular blade 24 cuts the protective film 20 and the photosensitive resin layer 18 into predetermined lengths, leaving the base film 16. Specifically, as shown in FIG. 4, the circular blade 24 forms partly cut regions 27a, 27b (see FIG. 2) in the form of slits in the protective film 20 and the photosensitive resin layer 18 at intervals that correspond to a length L of the photosensitive resin layer 18 to be pressure-bonded to a glass substrates 14 and widths M of protective films 20b to be left on the glass substrate 14.

In the label bonding mechanism 34, a label attracted by the suction pad 32 is bonded to the protective film 20 of the photosensitive sheet film 12 with the partly cut regions 27a, 27b formed therein. The label has its intermediate portion not bonded to the protective film 20b and its opposite ends bonded to the protective films 20a which will be peeled off from the photosensitive sheet film 12.

The photosensitive sheet film 12 with the label bonded thereto is supplied via the rollers 46 of the reservoir mechanism 36 to the peeling mechanism 38. In the peeling mechanism 38, the base film 16 of the photosensitive sheet film 12 is attracted by the suction drum 48, and the protective films 20a interconnected by the label are peeled off by the peeling roller 50 and wound by the takeup unit 52. As a result, protective films 20a are successively peeled off from the photosensitive sheet film 12, leaving protective films 20b having widths M corresponding to the spaces between glass substrates 14 on the photosensitive sheet film 12.

After the protective films 20a are peeled off, exposing corresponding portions of the photosensitive resin layer 18, the photosensitive sheet film 12 is supplied via the tension dancer 56 of the tension control mechanism 40 and the film bending roller 58 of the detecting mechanism 42 to a position between the pressure-bonding rollers 64a, 64b which are spaced from each other. When the leading end of the photosensitive sheet film 12 is to be positioned in place, i.e., when the photosensitive laminated body manufacturing apparatus 10 starts to operate, the leading end of the photosensitive sheet film 12 is gripped and fed by the film feed rollers 78 which is disposed downstream of the pressure-bonding rollers 64a, 64b.

A first glass substrate 14 is heated to a certain temperature by the substrate heater 66 of the substrate feed mechanism 62, and supplied at a timing described later to the position between the pressure-bonding rollers 64a, 64b which are spaced from each other.

When the partly cut region 27b of the photosensitive sheet film 12 which is detected by the detecting mechanism 42 reaches the position between the pressure-bonding rollers 64a, 64b and the leading end of the glass substrate 14 also reaches the position between the pressure-bonding rollers 64a, 64b, the elevating mechanism 72 is actuated to press the backup roller 70b upwardly to lift the pressure-bonding roller 64b, sandwiching the photosensitive sheet film 12 and the glass substrate 14 between the pressure-bonding rollers 64a, 64b. Then, the photosensitive sheet film 12 and the glass substrate 14 are fed while being pressed and heated by the pressure-bonding rollers 64a, 64b, whereupon the photosensitive resin layer 18 from which the protective film 20a has been peeled off is pressure-bonded to a predetermined area of the glass substrate 14.

Alternatively, after the photosensitive sheet film 12 and the glass substrate 14 are placed between the pressure-bonding rollers 64a, 64b, the photosensitive sheet film 12 and the glass substrate 14 may temporarily be stopped, or at least one of the photosensitive sheet film 12 and the glass substrate 14 may be moved at a low speed, and then pressure-bonded and fed while being sandwiched by the pressure-bonding rollers 64a, 64b.

When the leading end of the first glass substrate 14 to which the photosensitive resin layer 18 is transferred by the pressure-bonding rollers 64a, 64b approaches the film feed rollers 78, the film feed rollers 78 are spaced from the photosensitive sheet film 12, and the leading end of the photosensitive sheet film 12 which projects forwardly of the glass substrate 14 is cut off by the leading end cutting mechanism 74. Then, the glass substrate 14 with the photosensitive resin layer 18 transferred thereto is sandwiched and fed by the substrate feed rollers 80.

The photosensitive sheet film 12 between the glass substrate 14 which is continuously fed with the photosensitive resin layer 18 transferred thereto and the following glass substrate 14 is cut off and separated by the inter-substrate cutting mechanism 76 which is disposed downstream of the substrate feed rollers 80.

The photosensitive laminated body is thus constructed of the glass substrate 14 with the photosensitive resin layer 18 transferred thereto. After the base film 16 is peeled off from the photosensitive laminated body, the photosensitive laminated body is exposed to a certain pattern and then developed by photolithography. The same process is performed on photosensitive films having photosensitive material layers of different colors. In this manner, desired color filter substrates are manufactured.

In the present embodiment, in order to transfer the photosensitive resin layer 18 accurately to a predetermined position on the glass substrate 14 according to the positional relationship shown in FIG. 4, the detectors 60a, 60b disposed upstream of and closely to the pressure-bonding rollers 64a, 64b detect the partly cut regions 27a, 27b.

Specifically, after the protective film 20a, which is a part of the protective film 20, between the partly cut regions 27a, 27b has been peeled off from the photosensitive sheet film 12, the photosensitive sheet film 12 is supplied to the film bending roller 58 of the detecting mechanism 42. At this time, the photosensitive sheet film 12 is bent by the film bending roller 58 which changes the feeding direction of the photosensitive sheet film 12.

In each of the detectors 60a, 60b, the laser diode 39 is energized to apply the laser beam LB through the collimator lens 41 to the photosensitive sheet film 12. The optical axis of the laser beam LB emitted from the laser diode 39 is offset a predetermined distance OFF from the center of the film bending roller 58 toward the tension control mechanism 40 that is positioned upstream of the detecting mechanism 42. Therefore, the laser beam LB which is reflected by the surface of the photosensitive sheet film 12 is prevented from being applied to the amount-of-light sensor 45.

Figure 6:
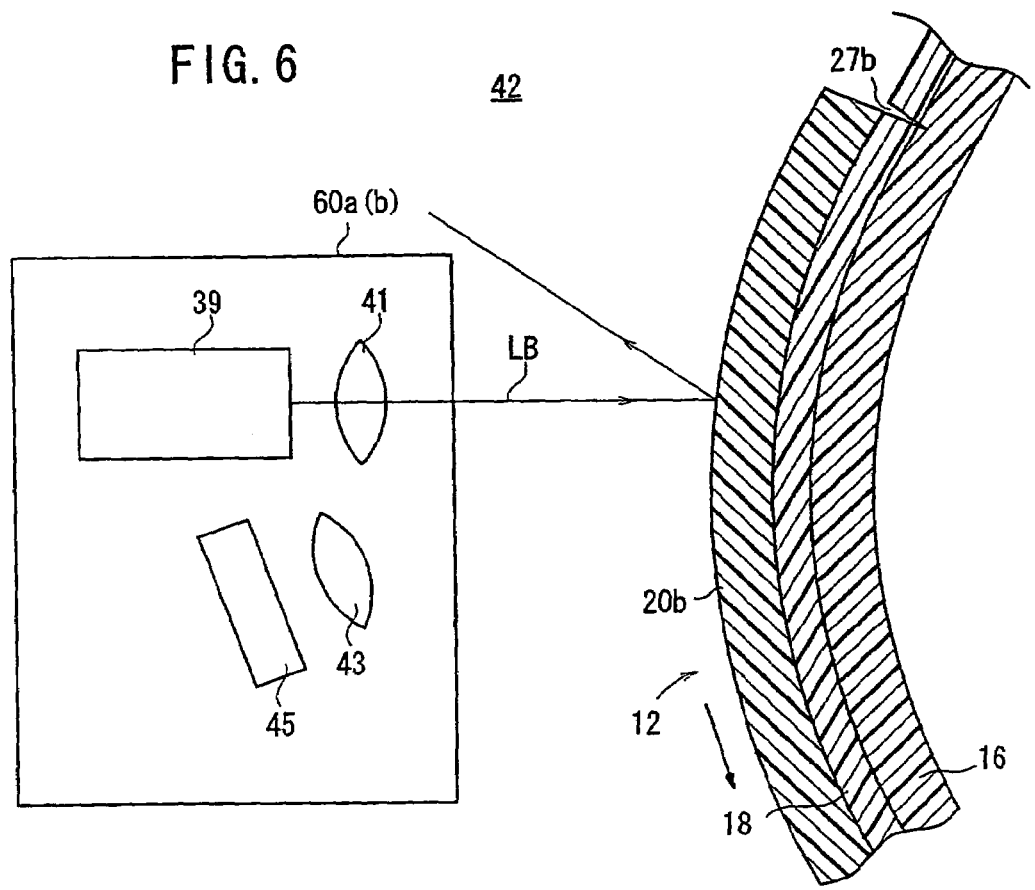
FIG. 6 is an enlarged schematic view showing the manner in which a partly cut region is detected by the detecting mechanism in the photosensitive laminated body manufacturing apparatus.

As shown in FIG. 6, when the protective film 20b remaining on the photosensitive sheet film 12 or the exposed area of the photosensitive resin layer 18 from which the protective film 20a has been peeled off moves across the optical axis of the laser beam LB, the laser beam LB which is reflected by the surface of the photosensitive sheet film 12 is not applied to the amount-of-light sensor 45. Similarly, the laser beam LB which passes through the photosensitive sheet film 12 and is reflected by the surface of the film bending roller 58 is not applied to the amount-of-light sensor 45.

Figure 7:
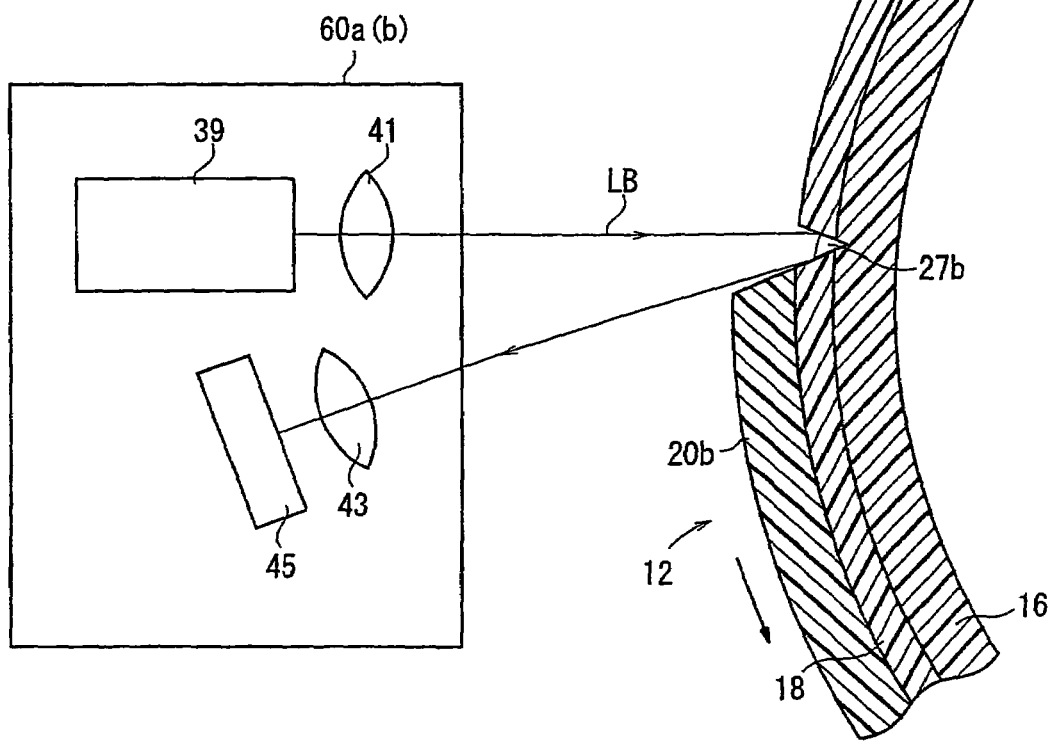
FIG. 7 is an enlarged schematic view showing the manner in which a partly cut region is detected by the detecting mechanism in the photosensitive laminated body manufacturing apparatus.

As shown in FIG. 7, when the partly cut region 27b (or 27a) of the photosensitive sheet film 12 moves across the optical axis of the laser beam LB, the laser beam LB is reflected and diffused by the partly cut region 27b (or 27a), and part of the reflected laser beam LB is applied through the condensing lens 43 to the amount-of-light sensor 45. Since the photosensitive sheet film 12 is bent by the film bending roller 58 so as to be convex toward the detectors 60a, 60b, the partly cut region 27b (or 27a) is spread widely, and part of the laser beam LB that is reflected and diffused by the widely spread partly cut region 27b (or 27a). Accordingly, the detectors 60a, 60b reliably detect when the partly cut region 27b (or 27a) passes through a certain position on the film bending roller 58.

FIG. 8 shows measured values of an amount of light reflected by the photosensitive sheet film 12 and detected by the amount-of-light sensor 45 when the predetermined distance OFF was 3 mm, the film bending roller 58 had a diameter of 40 mm, each of the partly cut regions 27a, 27b of the photosensitive sheet film 12 in a straight shape had a width of 20 μm, and the laser beam LB had a wavelength of 685 nm. As can be seen from FIG. 8, the detected amount of light has sharp peaks P1, P2 produced by the partly cut regions 27a, 27b. It will thus be understood that by positioning the film bending roller 58 and the detectors 60a, 60b as shown in FIG. 5, the detecting mechanism 42 can reliably detect the partly cut regions 27a, 27b in a reduced noise environment. The predetermined distance OFF and the diameter of the film bending roller 58 may vary depending on the conditions in which the detecting mechanism 42 is installed, and are not limited to the above values.

A control process for transferring the photosensitive resin layer 18 of the photosensitive sheet film 12 to the glass substrate 14 based on detected signals from the detectors 60a, 60b will be described below.

Amount-of-light signals detected by the respective amount-of-light sensors 45 of the two detectors 60a, 60b which are spaced axially along the film bending roller 58 are compared with a predetermined threshold TH1 (see FIG. 8). If the levels of the amount-of-light signals from the amount-of-light sensors 45 are greater than the threshold TH1, then a partly-cut-region detected signal indicating that the partly cut regions 27a, 27b are properly detected is output.

The levels of the amount-of-light signals detected by the amount-of-light sensors 45 differ depending on the color of the photosensitive resin layer 18 of the photosensitive sheet film 12. Therefore, the threshold TH1 may change to a different threshold TH2 if the photosensitive resin layer 18 has a different color. Instead, different laser diodes 39 may selectively be employed such that a blue laser beam LB will be applied to the photosensitive resin layer 18 which is red in color and a red laser beam LB will be applied to the photosensitive resin layer 18 which is blue in color, for example.

If the level of the amount-of-light signal from only one of the amount-of-light sensors 45 is greater than the threshold TH1 (or the threshold TH2), or if the output timing of the amount-of-light signals from the amount-of-light sensors 45 is different, then it is judged that the operation or the setting of the detectors 60a, 60b is suffering a failure or foreign matter such as dust is applied to a portion of the photosensitive sheet film 12. A failure detected signal is output to display a failure message on a display unit, issue an alarm signal, and generate defective product removal information for a subsequent process. Alternatively, a failure process for shutting off the photosensitive laminated body manufacturing apparatus 10 in emergency is performed to prevent defective products from being produced.

If the partly cut regions 27a, 27b are properly detected, the timing to supply the glass substrate 14 is adjusted depending on the period of time that is consumed until the partly cut regions 27a, 27b reaches a given position between the film bending roller 58 and the pressure-bonding rollers 64a, 64b, and then the glass substrate 14 is supplied to the position between the pressure-bonding rollers 64a, 64b at the adjusted timing. As a result, based on the partly cut regions 27a, 27b, the photosensitive resin layer 18 of the photosensitive sheet film 12 from which the protective film 20a has been peeled off is accurately transferred to the desired position on the glass substrate 14.

Rather than adjusting the timing to supply the glass substrate 14 to the pressure-bonding rollers 64a, 64b based on the time when the partly cut regions 27a, 27b are properly detected, the photosensitive sheet film 12 may be fed a certain length after the partly cut regions 27a, 27b are detected, the partly cut regions 27a, 27b may be stopped in position between the pressure-bonding rollers 64a, 64b, and thereafter the glass substrate 14 may be supplied to the position between the pressure-bonding rollers 64a, 64b to transfer the photosensitive resin layer 18 to the glass substrate 14.

Based on the detected signals output from the detectors 60a, 60b as representing the partly cut regions 27a, 27b, the following two measuring processes may be performed.

According to the first measuring process, the glass substrate 14 is clamped by the pressure-bonding rollers 64a, 64b, and the number of pulses generated by an encoder combined with a drive motor (not shown) for rotating the pressure-bonding rollers 64a, 64b, as representing the distance by which the glass substrate 14 is fed from the start of rotation of the pressure-bonding rollers 64a, 64b, is compared with the preset number of pulses generated when the partly cut region 27b is to be detected by the detecting mechanism 42, thereby measuring a displacement of a leading partly cut region 27b. If the partly cut region 27b is detected before the preset number of pulses is reached, then the partly cut region 27b is judged as being displaced forwardly of a predetermined position on the glass substrate 14 by a distance indicated by the difference between the numbers of pulses. Conversely, if the partly cut region 27b is detected after the preset number of pulses is reached, then the partly cut region 27b is judged as being displaced rearwardly of a predetermined position on the glass substrate 14.

According to the second measuring process, the number of pulses generated by an encoder combined with a drive motor (not shown) for rotating the pressure-bearing rollers 64a, 64b is measured from the detection of a leading partly cut region 27b to the detection of a trailing partly cut region 27a, thereby measuring the laminated length (length L) of the photosensitive sheet film 12. The preset number of pulses corresponding to the length L under normal conditions of the photosensitive sheet film 12 is compared with the actually measured number of pulses. If the actually measured number of pulses is greater than the preset number of pulses, then the photosensitive sheet film 12 is judged as being stretched due to heat or the like by a distance indicated by the difference between the numbers of pulses. If the actually measured number of pulses is smaller than the preset number of pulses, then the photosensitive sheet film 12 is judged as being shorter than normal by a distance indicated by the difference between the numbers of pulses.

If the leading end of the photosensitive resin layer 18 is detected as being displaced (advanced) forward with respect to a joined range of the glass substrate 14 according to the first measuring process, then the relative positions of the glass substrate 14 and the partly cut region 27b of the photosensitive sheet film 12 are adjusted.

Specifically, if the partly cut region 27b detected by the detectors 60a, 60b is detected as being advanced from a predetermined position, then the film feed rollers 78 feed an unjoined portion of the photosensitive sheet film 12 by a distance represented by the difference between the preset distance and the advanced distance. As a result, the partly cut region 27b is positionally adjusted and placed in a predetermined position between the pressure-bonding rollers 64a, 64b. Thereafter, the glass substrate 14 is delivered under normal delivery control between the pressure-bonding rollers 64a, 64b, and the photosensitive resin layer 18 is joined at a normal position to the glass substrate 14, i.e., in the joined range of the glass substrate 14.

If the partly cut region 27b detected by the detectors 60a, 60b is detected as being delayed from the joined range of the glass substrate 14, then the substrate feed rollers 80 feed an unjoined portion of the photosensitive sheet film 12 by a distance represented by the sum of the preset distance and the delayed distance.

Rather than adjusting the distance that the glass substrate 14 is fed by the substrate feed rollers 80, the substrate feed mechanism 62 may be controlled to adjust the position at which the glass substrate 14 is to be stopped, by the advanced or delayed distance.

The distance between the partly cut regions 27a, 27b detected by the detectors 60a, 60b, i.e., the length L of the photosensitive resin layer 18 to be joined to the glass substrate 14, is measured according to the second measuring process. If the length L is greater than the joined range of the glass substrate 14, then the positions of the partly cut regions 27a, 27b are changed so that the distance between the partly cut regions 27a, 27b, i.e., the length L, is reduced by the difference. If the length L is smaller than the joined range of the glass substrate 14, then the positions of the partly cut regions 27a, 27b are changed so that the distance between the partly cut regions 27a, 27b, i.e., the length L, is increased by the difference. In this manner, the length L of the photosensitive resin layer 18 is adjusted to a predetermined length.

It is also possible to change the amount of stretch of the photosensitive sheet film 12 by adjusting the tension of the photosensitive sheet film 12 with the tension dancer 56 of the tension control mechanism 40.

Consequently, the partly cut regions 27a, 27b of the photosensitive sheet film 12 can be positioned highly accurately with respect to the joining position, allowing the photosensitive resin layer 18 of the photosensitive sheet film 12 to be joined accurately with respect to the desired area of the glass substrate 14. It is thus possible to efficiently manufacture a high-quality photosensitive laminated body through a simple process and arrangement.

In the embodiment described above, the photosensitive sheet film 12 is bent by the film bending roller 58 so as to be convex toward the detectors 60a, 60b, spreading the partly cut regions 27a, 27b to allow themselves to be detected reliably. However, the photosensitive sheet film 12 may be bent by a bending member having a corner so as to be convex toward the detectors 60a, 60b, spreading the partly cut regions 27a, 27b. Alternatively, the photosensitive sheet film 12 may be pulled in the vicinity of the detectors 60a, 60b to spread the partly cut regions 27a, 27b.

In the illustrated embodiment, the laser diode 39 for emitting the laser beam LB and the amount-of-light sensor 45 for detecting the amount of light of the laser beam LB are used respectively as an illuminating means and a light-detecting means for detecting the partly cut regions 27*a*, 27*b*. Instead, an illuminating means for uniformly illuminating the photosensitive sheet film 12 bent by the film bending roller 58 and an image capturing means such as a one-dimensional or two-dimensional CCD camera or the like for capturing image information of a bent region of the illuminated photosensitive sheet film 12 may be provided, and the positions of the partly cut regions 27*a*, 27*b* in captured image information of the photosensitive sheet film 12 may be calculated.

If the photosensitive sheet film 12 is made of a light-permeable material, then the surface of the film bending roller 58 may comprise a diffusive reflecting surface for preventing the illuminating light reflected by the surface of the film bending roller 58 from being directly applied to the image capturing means, so that the amount-of-light sensors 45 may have a sufficient dynamic range for detecting the partly cut regions 27*a*, 27*b*. Alternatively, the surface of the film bending roller 58 may comprise a light absorbing surface such as a black surface for absorbing the illuminating light.

Although a certain preferred embodiment of the present invention has been shown and described in detail, it should be understood that various changes and modifications may be made therein without departing from the scope of the appended claims.

The invention claimed is:

1. A detecting device which detects a recess purposely formed in a sheet body which defines a peeled laminate region of said sheet body exposed to be boned with a substrate, comprising:
   spreading means which deforms said sheet body to spread said recess;
   illuminating means which applies illuminating light to said sheet body with said recess being spread by said spreading means; and
   light-detecting means which detects said illuminating light reflected by said sheet body;
   wherein said recess is detected based on said illuminating light detected by said light-detecting means.

2. A detecting device according to claim 1, wherein said spreading means comprises pulling means which pulls said sheet body.

3. A detecting device according to claim 2, wherein said pulling means comprises deforming means which presses said sheet body from one surface thereof toward an opposite surface thereof which has said recess defined therein to bend said sheet body toward said opposite surface;
   said illuminating means illuminates said opposite surface of said sheet body; and
   said light-detecting means detects said illuminating light reflected from said opposite surface of said sheet body.

4. A detecting device according to claim 3, wherein said deforming means comprises a roller which presses said sheet body along a direction in which said recess extends.

5. A detecting device according to claim 4, wherein said sheet body is made of a light-permeable material, said roller having a diffusive reflecting surface.

6. A detecting device according to claim 4, wherein said sheet body is made of a light-permeable material, said roller having a light absorbing surface.

7. A detecting device according to claim 1, wherein said sheet body comprises a plurality of laminated sheet layers, said recess comprising a partly cut region formed by cutting into said sheet layers except at least one sheet layer.

8. A detecting device according to claim 1, wherein said illuminating means comprises a laser which applies a laser beam to said sheet body, and said light-detecting means is disposed in a position which is offset a predetermined distance from an area for detecting said laser beam reflected from a surface of said sheet body other than said recess.

9. A detecting device according to claim 1, wherein said light-detecting means comprises image capturing means which captures image information of said sheet body, and said recess is detected based on said image information.

10. A detecting device according to claim 9, wherein said image capturing means comprises a CCD sensor.

11. A detecting device according to claim 1, wherein said light-detecting means comprises an amount-of-light sensor which detects an amount of said illuminating light.

12. A detecting device according to claim 1, wherein said light-detecting means comprises a position sensor which detects a position to which said illuminating light reflected by said sheet body is applied.

13. A detecting device according to claim 1, wherein said light-detecting means comprises a plurality of light-detecting means spaced along a direction in which said recess extends.

14. A detecting device according to claim 1, wherein said sheet body has a colored layer, and said recess is formed by cutting into said colored layer.

15. A detecting device according to claim 14, wherein said light-detecting means has a thresholds which can selectively be used to detect said recess depending on a color of said colored layer.

16. An apparatus for manufacturing a laminated body by forming a recess in a predetermined area of a sheet body having a plurality of laminated sheet layers, supplying said sheet body to a substrate, and laminating said sheet body onto said substrate based on said recess, comprising:
   a detecting unit which detects said recess; and
   a laminating unit disposed downstream of said detecting unit, which laminates said sheet body onto said substrate;
   said detecting unit comprising:
      spreading means which deforms said sheet body to spread said recess;
      illuminating means which applies illuminating light to said sheet body with said recess being spread by said spreading means; and
      light-detecting means which detects said illuminating light reflected by said sheet body;
      wherein said recess is detected based on said illuminating light detected by said light-detecting means.

17. An apparatus according to claim 16, further comprising a tension controller disposed upstream of said detecting unit, which controls tension applied to said sheet body.

18. An apparatus according to claim 16, wherein said laminating unit comprises thermal pressure-bonding means which heats said sheet body to a predetermined temperature and pressure-bonding said sheet body to said substrate.

19. An apparatus according to claim 18, wherein said detecting unit is housed in a heat-insulating case.

20. An apparatus according to claim 16, wherein said spreading means comprises a roller which bends said sheet body so as to be convex toward said detecting unit and feeding said sheet body to said laminating unit.

* * * * *